US012336795B2

(12) United States Patent
Plicchi

(10) Patent No.: US 12,336,795 B2
(45) Date of Patent: Jun. 24, 2025

(54) DEVICE FOR VENOUS-PRESSURE SENSING

(71) Applicant: TRE ESSE Progettazione Biomedica S.r.l., Bologna (IT)

(72) Inventor: Gianni Plicchi, Bologna (IT)

(73) Assignee: TRE ESSE Progettazione Biomedica S.r.l., Bologna (IT)

( * ) Notice: Subject to any disclaimer, the term of this patent is extended or adjusted under 35 U.S.C. 154(b) by 914 days.

(21) Appl. No.: 17/421,260

(22) PCT Filed: May 28, 2020

(86) PCT No.: PCT/IB2020/055060
§ 371 (c)(1),
(2) Date: Jul. 7, 2021

(87) PCT Pub. No.: WO2020/260981
PCT Pub. Date: Dec. 30, 2020

(65) Prior Publication Data
US 2022/0022764 A1     Jan. 27, 2022

(30) Foreign Application Priority Data
Jun. 27, 2019 (IT) .......................... 102019000010248

(51) Int. Cl.
*A61B 5/0225* (2006.01)
*A61B 5/00* (2006.01)
(Continued)

(52) U.S. Cl.
CPC ...... *A61B 5/02255* (2013.01); *A61B 5/02141* (2013.01); *A61B 5/0535* (2013.01); *A61B 5/6824* (2013.01); *A61B 2562/0247* (2013.01)

(58) Field of Classification Search
CPC . A61B 5/02141; A61B 5/022; A61B 5/02255; A61B 2562/0247; A61B 5/0535; A61B 5/6824; A61B 5/7246
See application file for complete search history.

(56) References Cited

U.S. PATENT DOCUMENTS 4,924,873 A * 5/1990 Sorensen ............... A61B 5/022
                                                          600/498
5,464,019 A * 11/1995 Anderson ........... A61B 5/0235
                                                          600/490
(Continued)

FOREIGN PATENT DOCUMENTS

CN        101692975 A      4/2010
CN        103976722 A      8/2014
(Continued)

OTHER PUBLICATIONS

Amar, David, et al., "Correlation of Peripheral Venous Pressure and Central Venous Pressure in Surgical Patients", Journal of Cardiothoracic and Vascular Anesthesia, vol. 15, No. 1, Feb. 2001, pp. 40-43.
(Continued)

*Primary Examiner* — Charles A Marmor, II
*Assistant Examiner* — Andrew E Hoffpauir
(74) *Attorney, Agent, or Firm* — Nixon & Vanderhye P.C.

(57) ABSTRACT

A device for non-invasive venous-pressure sensing comprises an occlusive element (OC) configured to be applied to a proximal portion of a human limb in order to apply an occlusion pressure thereto, and a dilation-sensing element (VS) configured to be applied to a distal portion of a human limb in order to detect an extent of dilation thereof. The device likewise comprises a control circuit (10) coupled to the occlusive element (OC) and to the dilation-sensing element (VS). The control circuit (10) is configured to: —i) control (104, 106) the occlusive element (OC) in order to apply at least one sub-diastolic occlusion pressure and maintain it for a certain occlusion interval; —ii) obtain (108a, 108b) from the dilation-sensing element (VS) a sensing signal; —iii) carry out a check on the sensing signal for a certain variation of the dilation of the distal portion resulting from the fact that the occlusion pressure is removed; and —iv) issue a signal (102) indicating a venous
(Continued)

pressure that is lower than the applied occlusion pressure (P0c) as a result of the fact that said check indicates a variation in the dilation of the distal portion of the limb resulting from the fact that the occlusion pressure has been removed.

13 Claims, 5 Drawing Sheets

(51) Int. Cl.
    *A61B 5/021*     (2006.01)
    *A61B 5/0535*     (2021.01)

(56) References Cited

U.S. PATENT DOCUMENTS

| | | | | |
|---|---|---|---|---|
| 5,485,838 | A * | 1/1996 | Ukawa | A61B 5/6826 356/41 |
| 2004/0044290 | A1 * | 3/2004 | Ward | A61B 5/022 600/490 |
| 2004/0059234 | A1 * | 3/2004 | Martin | A61B 5/024 600/500 |
| 2005/0240109 | A1 * | 10/2005 | Inoue | A61B 5/02141 600/490 |
| 2009/0326392 | A1 * | 12/2009 | Kolluri | A61B 5/02225 600/490 |
| 2010/0292592 | A1 | 11/2010 | Parfenov et al. | |
| 2014/0135634 | A1 * | 5/2014 | Pranevicius | A61B 5/02225 600/492 |
| 2015/0099953 | A1 * | 4/2015 | Baker, Jr. | A61B 5/14552 600/324 |
| 2016/0175184 | A1 * | 6/2016 | Arkans | A61H 23/0263 601/149 |

FOREIGN PATENT DOCUMENTS

| | | |
|---|---|---|
| CN | 107530223 A | 1/2018 |
| JP | 2001-309895 A | 11/2001 |
| JP | 2010-279654 A | 12/2010 |
| JP | 2012-205822 A | 10/2012 |
| WO | 2017/022245 A1 | 2/2017 |

OTHER PUBLICATIONS

Bauer, A., et al., "Influence of different cuff inflation protocols on capillary filtration capacity in human calves—a congestion plethysmography study", Journal of Physiology, vol. 543.3, Sep. 2002, pp. 1025-1031.

Christ, F., et al., "Relationship between venous pressure and tissue vol. during venous congestion plethysmography in man", Journal of Physiology, vol. 503.2, Sep. 1997, pp. 463-467.

Desjardins, Roger, et al., "Can peripheral venous pressure be interchangeable with central venous pressure in patients undergoing cardiac surgery?", Intensive Care Medicine, vol. 30, 2004, pp. 627-632.

Gamble, John, et al., "A Reassessment of Mercury in Silastic Strain Guage Plethysmography for Microvascular Permeability Assessment in Man", Journal of Physiology, vol. 464, May 1993, pp. 407-422.

Halliwill, John R., et al., "Measurement of limb venous compliance in humans: technical considerations and physiological findings", Journal of Applied Physiology, vol. 87, No. 4, Oct. 1999, pp. 1555-1563.

Jassim, Haitham Mohammed, et al., "IJV collapsibility index vs IVC collapsibility index by point of care ultrasound for estimation of CVP: a comparative study with direct estimation of CVP", Open Access Emergency Medicine 2019, vol. 11, pp. 65-75.

Sathish, N., et al., "Comparison between noninvasive measurement of central venous pressure using near infrared spectroscopy with an invasive central venous pressure monitoring in cardiac surgical Intensive Care Unit", Annals of Cardiac Anaesthesia, vol. 19, Issue 3, Jul.-Sep. 2016, pp. 405-409.

Thalhammer, Christoph, et al., "Noninvasive Central Venous Pressure Measurement by Controlled Compression Sonography at the Forearm", Journal of the American College of Cardiology, vol. 50, No. 16, Oct. 16, 2007, pp. 1584-1589.

Thalhammer, Christoph, et al., "Non-invasive central venous pressure measurement by compression ultrasound—A step into real life", Resuscitation, vol. 80, No. 10, 2009, pp. 1130-1136.

Ward, Kevin R., et al., "A new noninvasive method to determine central venous pressure", Resuscitation, vol. 70, No. 2, Aug. 2006, pp. 238-246.

Ward, Kevin R., et al., "A Novel Noninvasive Impedance-Based Technique for Central Venous Pressure Measurement," SHOCK, vol. 33, No. 3, Mar. 2010, pp. 269-273.

Office Action dated Nov. 28, 2023, issued in Japan Patent Application No. 2021-541306, 5 pages.

Jan T. Groothius, et al., "Venous cuff pressures from 30 mmHg to diastolic pressure are recommended to measure arterial inflow by plethysmography", Journal of Applied Physiology, vol. 95, published Apr. 4, 2003, pp. 342-347 (6 pages).

International Search Report for PCT/IB2020/055060 dated Jul. 13, 2020, 4 pages.

Written Opinion of the ISA for PCT/IB2020/055060 dated Jul. 13, 2020, 6 pages.

First Office Action for Chinese Application 2020800089663, 13 pages, dated Jul. 6, 2024.

* cited by examiner

DEVICE FOR VENOUS-PRESSURE SENSING

TECHNICAL FIELD

This application is the U.S. national phase of International Application No. PCT/IB2020/055060 filed May 28, 2020 which designated the U.S. and claims priority to IT patent application No. 102019000010248 filed Jun. 27, 2019, the entire contents of each of which are hereby incorporated by reference.

The present disclosure relates to detection (measurement) of venous pressure (VP).

One or more embodiments may refer to devices for non-invasive venous-pressure sensing that can be used not only by staff specialised in the clinical field but also by the patients themselves at home.

TECHNOLOGICAL BACKGROUND

Venous pressure at the right atrium, referred to as central venous pressure (CVP), represents an indirect indicator of blood volume and pressure of filling of the right ventricle, thus proving to be a haemodynamic parameter useful for diagnosis and management of the therapy of patients with cardiac decompensation and pathologies of the splanchnic district. Up to now, for the measurement of CVP, in intensive care units techniques of an invasive type are widely used, which are based upon insertion of disposable catheters connected to a pressure transducer in a deep vein of large calibre, the subclavian vein, the jugular vein, or the basilic vein. Such procedures may prove costly, not well tolerated, and not without risks for the patient.

There exists, on the other hand, a quite extensive literature regarding non-invasive methods for evaluating CVP.

Examples of this literature are documents such as:

Thalhammer C., et al., "Noninvasive central venous pressure measurement by controlled compression sonography at the forearm", J. Amer. College Cardiol., vol. 50, no. 16, pp. 1584-1589, 2007;

Thalhammer C., et al., "Non-invasive central venous pressure measurement by compression ultrasound—A step into real life", Resuscitation, vol. 80, no. 10, pp. 1130-1136, 2009;

Amar D., Melendez J. A., Zhang H., Dobres C., Leung D. H., Padilla R. E., "Correlation of peripheral venous pressure and central venous pressure in surgical patients", J. Cardiothorac. Vasc. Anesth., 2001; 15: 40-3;

Desjardins R., Denault A. Y., Belisle S., et al. "Can peripheral venous pressure be interchangeable with central venous pressure in patients undergoing cardiac surgery?", Intensive Care Med. 2004; 30: 627-32;

Sathish N., "Comparison between noninvasive measurement of central venous pressure using near-infrared spectroscopy with an invasive central venous pressure monitoring in cardiac surgical Intensive Care Unit", Ann. Card. Anaesth. 2016 July-September; 19(3): 405-409;

Jassim, H. M., "IJV collapsibility index vs IVC collapsibility index by point of care ultrasound for estimation of CVP: a comparative study with direct estimation of CVP", Open Access Emerg. Med. 2019; 11: 65-75;

Ward K. R., et al., "A new noninvasive method to determine central venous pressure", Resuscitation, 2006 August; 70(2): 238-46. Epub 2006 Jul. 3;

Ward K. R., et al., "A novel noninvasive impedance-based technique for central venous pressure measurement", Shock, 2010 March; 33(3): 269-73; doi: 10.1097/SHK.0b013e3181ab9b9b;

Halliwill J. R., et al., "Measurement of limb venous compliance in humans: technical considerations and physiological findings", J. Appl. Physiol. (1985), 1999 October; 87(4): 1555-63;

Christ F., et al., "Relationship between venous pressure and tissue volume during venous congestion plethysmography in man", J. Physiol. 1997 Sep. 1; 503 (Pt. 2): 463-7;

Gamble J. F., et al., "A reassessment of mercury in silastic strain gauge plethysmography for microvascular permeability assessment in man", J. Physiol. 1993 May; 464: 407-22;

Bauer A., et al., "Influence of different cuff inflation protocols on capillary filtration capacity in human calves—a congestion plethysmography study", J. Physiol. 2002 Sep. 15; 543(Pt 3): 1025-1031.

Apparatuses and methods for non-invasive measurement of CVP have likewise been proposed and described in prior-art patents and patent applications.

For instance, documents such as: U.S. Pat. No. 7,118,534 B2 (which corresponds to US2004/0044290 A1), US 2012/253209 A1, WO 2017/022245 A1, U.S. Pat. No. 6,432,061 B1, U.S. Pat. No. 4,566,462 A, US 2007/0239041 A1, U.S. Pat. Nos. 5,040,540 A, 8,417,306 B2, US 2017/0100044 A1 or U.S. Pat. No. 5,904,142 A describe various solutions for the non-invasive measurement of CVP.

In particular, in U.S. Pat. No. 7,118,534 B2/US2004/0044290 A1 central venous pressure (CVP) is identified simply as a synchronous correspondence between the occlusion pressure $P_{oc}$ and the curve of the volume (which is the expression of the Rapid Volume Response, RVR, in the forearm following upon the occlusion pressure $P_{oc}$ applied) during deflation of the occlusive cuff and after applying a single step of the pressure $P_{oc}$ at 40-60 mmHg, with the CVP being determined on the basis of the pressure at the maximum slope of the curve of variation of the volume. This synchronous analysis does not take into account the physiological time constant associated to the RVR, which is dependent upon the specific vein/tissue compliance of the patient and determines a variable temporal shift between the occlusive action (i.e., the pressure signal) and the effect of this action (i.e., the volume signal), thus introducing inexactitudes in the determination of the CVP due to the variable temporal relation between the curves of the occlusion pressure and of the volume.

On the other hand, also known, for example from documents such as U.S. Pat. No. 7,524,290 B2, 4,204,545 A, 5,447,161 A, 6,322,515 B1, 9,474,453 B2, 6,916,289 B2 or 6,749,567 B2, are various non-invasive systems for measuring the flows/pressures of the blood, with particular attention paid to the technique of occlusive plethysmography typically used for measurement of the district flows (at the level of the limbs). This technique may envisage the use of an occlusive cuff positioned around the limb in question and of an instrument for measuring the variations in volume (generally referred to as "plethysmograph") induced in the distal part of the limb, positioned downstream of the occlusive cuff. The measuring plethysmograph may be obtained with various systems, including strain gauges, photoplethysmographic sensors, impedance meters, pneumatic cuffs for pressure measurements, inductive systems, and capacitive systems.

In the case of the technique known as venous occlusive plethysmography (VOP), the occlusive cuff is inflated to a pressure lower than the diastolic arterial pressure but higher than the venous pressure (range: 40-60 mmHg) to enable flow of arterial blood to the limb but limit venous return thereof and consequently increase the pre-existing venous pressure. The portion of limb and the venous volume are consequently subject to a positive variation in volume detected by the plethysmograph.

For instance, the document U.S. Pat. No. 5,447,161 A describes photoplethysmographic techniques, i.e., a VOP where the plethysmograph applied to the limb of interest is provided as a photoplethysmograph that measures the changes of the blood volume of the superficial veins underlying the reflection photoplethysmograph, which dilate as a result of the pressure exerted by the occlusive cuff.

Again, documents such as U.S. Pat. Nos. 5,089,961 A, 9,125,569 B2, U52010/0292586 A1 or U.S. Pat. No. 6,309,359 B1, describe techniques of so-called air plethysmography, i.e., a VOP where the plethysmograph applied to the limb of interest is provided as a pneumatic cuff associated to a pressure transducer, exploiting the fact that, in a closed system, volume and pressure are inversely proportional to one another and the fact that the volume of air in the pneumatic cuff is equivalent (but with opposite sign) to the volume of the limb around which it is wrapped. Consequently, the pressure in the pneumatic cuff is directly proportional to the volume of the limb in question.

It may hence be noted that in the prior art there have already be proposed various solutions for non-invasive monitoring of venous pressure (VP), based, for example, upon the so-called venous occlusive plethysmography (VOP), which envisages the use of an occlusive cuff wrapped around the limb in question and of an instrument for measuring the variations in volume (generally referred to as "plethysmograph") induced in the distal part of the limb, positioned downstream of the occlusive cuff.

In brief, in VOP the occlusive cuff is inflated to a pressure (typically 40 mmHg) such as to exceed the venous pressure and hence limit venous return from the stretch of limb downstream of the occlusive cuff, which thus undergoes swelling (variation in volume), which is detected by the plethysmograph. As has been said, the plethysmograph may be obtained with various systems, including strain gauges, photoplethysmographic sensors, impedance meters, pneumatic cuffs for pressure measurements, inductive systems, and capacitive systems.

From an analysis of the prior art discussed previously it may, however, be noted that many methods based upon the VOP technique entail an evaluation based upon the temporal correspondence between events computed on the curve of volumetric variation of the limb or of the veins that is obtained in response to the occlusion and events that occur on the occlusion-pressure curve during the dynamic steps of pressurization and pressure release.

In practice, there may, however, be noted the occurrence of a phase offset between the occlusion-pressure curve and the curve of variation of volume of the limb and of the veins, which is not constant and depends upon the vein/tissue compliance of the specific subject (and corresponding time constant). The vein/tissue compliance presents a wide variability from subject to subject (and also from measurement to measurement on one and the same subject), so that it is in effect extremely difficult to associate uniquely an event in the volume curve to the corresponding measurement of the occlusion pressure to which the estimated value of venous pressure should correspond.

Consequently, these methods prove far from reliable.

OBJECT AND SUMMARY

The object of one or more embodiments is thus to provide a fast and reliable tool for monitoring CVP in a non-invasive way without the need for a central venous access, with the consequent possibility of its use, not only by staff specialised in the clinical field, but also by the patients themselves at home.

According to one or more embodiments, the above object may be achieved thanks to a device having the characteristics recalled in the ensuing claims.

The claims form an integral part of the technical teachings provided herein in relation to the embodiments.

One or more embodiments may provide a device for non-invasive sensing (for example, measurement) of venous pressure (VP) that will be able to overcome the main problems of the solutions so far known, regarding in particular the low accuracy of the measurement and the possible use (also) for home monitoring without the intervention of a specialist physician.

One or more embodiments may exploit widely documented results of physio-pathological research on vein compliance of the limbs in human beings (see, for example, the papers by Halliwill J. R. et al., Christ F. et al., Gamble J. et al., Bauer A. et al. already cited at an outset) for whom, when a cuff is used around the arm, the pressure applied by the cuff represents the venous pressure (VP) obtained in the forearm in the case where the pressure applied is higher than VP.

One or more embodiments may consequently envisage application of a known pressure ($P_{OC}$) via an occlusive cuff that surrounds the top portion of an arm that includes a vein, producing in the forearm an artificially induced venous pressure having the same value as the pressure $P_{OC}$.

In the use of one or more embodiments, by inflating the occlusive cuff with known increasing steps of pressure $P_{OC}$ and comparing at each step the rapid volume response (RVR) in the forearm caused by the artificially induced venous pressure with the pre-existing natural volume of the limb, it is possible to determine the value of VP from an ON/OFF analysis carried out on the RVR signal that can be measured by means of a volume sensor (extent of dilation) of a type in itself known, such as, to provide two possible examples, another sensing cuff that can supply a pressure signal $P_{SC}$ or else a photoplethysmographic sensor that supplies an indication of the variations in the volume of the underlying superficial veins $V_{VS}$, after release of the occlusion.

For instance:

if there is an appreciable drop in the pressure signal $P_{SC}$ (drop beyond a programmable threshold, e.g., 0.1 mmHg) or in the volume signal $V_{VS}$, expression of a reduction in the RVR, which is a consequence of the fact that the VP of the patient is lower than the value of the occlusion pressure $P_{OC}$ applied, the device will be able to indicate that the VP is lower than X mmHg (with X mmHg corresponding to the pressure value $P_{OC}$ set for the test);

otherwise, i.e., in the case where no appreciable drop is detected in the pressure signal $P_{SC}$ (a drop below the aforesaid threshold) or in the volume signal $V_{VS}$, as a result of the fact that the VP of the patient is higher than the value of the occlusion pressure $P_{OC}$ applied, the device will be able to indicate that the VP is higher than X mmHg (OFF response).

Added to the above is the possibility of repeating, automatically or after prior consent, testing with a subsequent (higher) value, of XX mmHg, of the pressure $P_{OC}$ programmed by the system.

It will on the other hand be appreciated that reference, for simplicity of illustration, to an upper limb (arm) is not to be understood as in any way limiting the embodiments.

One or more embodiments may in fact be applied to different areas of the body, for example to a lower limb (leg), with a solution that may prove particularly advantageous for a patient in bed.

BRIEF DESCRIPTION OF THE DRAWINGS

One or more embodiments will now be described, purely by way of non-limiting example, with reference to the annexed drawings, wherein.

DETAILED DESCRIPTION OF EXAMPLES OF EMBODIMENTS

Figure 1:
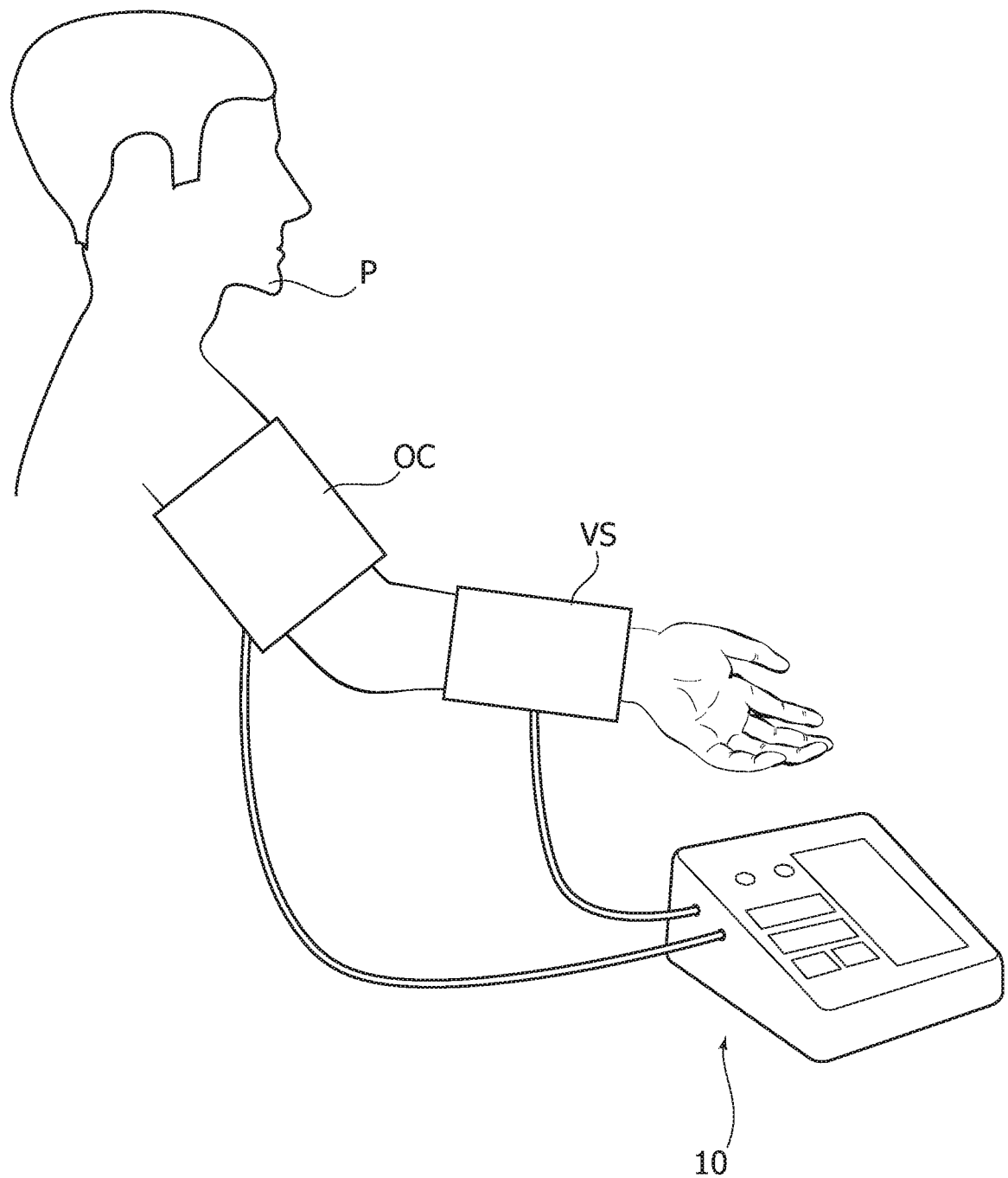
FIG. 1 represents a possible modality of implementation of a device according to some embodiments.

In the ensuing description, various specific details are illustrated, in order to enable an in-depth understanding of various examples of embodiments according to the description. The embodiments may be obtained without one or more of the specific details, or with other methods, components, materials, etc. In other cases, known operations, structures, or materials are not illustrated or described in detail so that the various aspects of the embodiments will not be obscured.

Reference to "an embodiment" or "one embodiment" in the framework of the present description is intended to indicate that a particular configuration, structure, or characteristic described in relation to the embodiment is comprised in at least one embodiment. Hence, phrases such as "in an embodiment" or "in one embodiment" that may be present in various points of the present description do not necessarily refer exactly to one and the same embodiment. Moreover, particular conformations, structures, or characteristics may be combined in any adequate way in one or more embodiments.

The references used herein are provided merely for convenience and hence do not define the sphere of protection or the scope of the embodiments.

Basically, a device according to some embodiments as exemplified herein (see, for example, FIGS. 1 and 4) may comprise:

an occlusion element OC and an element VS for sensing (detecting) dilation that can be arranged, respectively, on the proximal stretch and on the distal stretch of a limb of a subject (patient) P subjected to venous-pressure sensing; and a signal-processing circuit 10 coupled to the occlusion element OC and to the dilation-sensing element VS.

As has already been said, reference, for simplicity of illustration, to an upper limb (arm) is not to be understood as in any way limiting the embodiment: one or more embodiments may in fact be applied to different areas of the body, for example to a lower limb (leg).

Likewise, reference, once again for simplicity of illustration, to a "patient" is not to be understood as in any sense limiting the possible context of use of the embodiments: one or more embodiments may, in fact, be applied to contexts of use where the patient P subjected to venous-pressure sensing is not affected by an evident pathological condition, the person possibly being, for example, an athlete subjected to venous-pressure sensing to obtain indications on his or her athletic performance.

Again, as will be described more fully in what follows, both the occlusion element OC and the dilation-sensing element VS may be obtained with different technological solutions and may be provided either as distinct elements (as is illustrated herein by way of example) or as elements integrated with one another, with the possibility of maintaining their respective functions.

Finally, it will be noted that coupling of the occlusion element OC and of the dilation-sensing element VS to the processing circuit 10, here exemplified as implemented via cables or wires, may be obtained also in wireless form (for example, via Bluetooth interfaces or the like).

Figure 2:
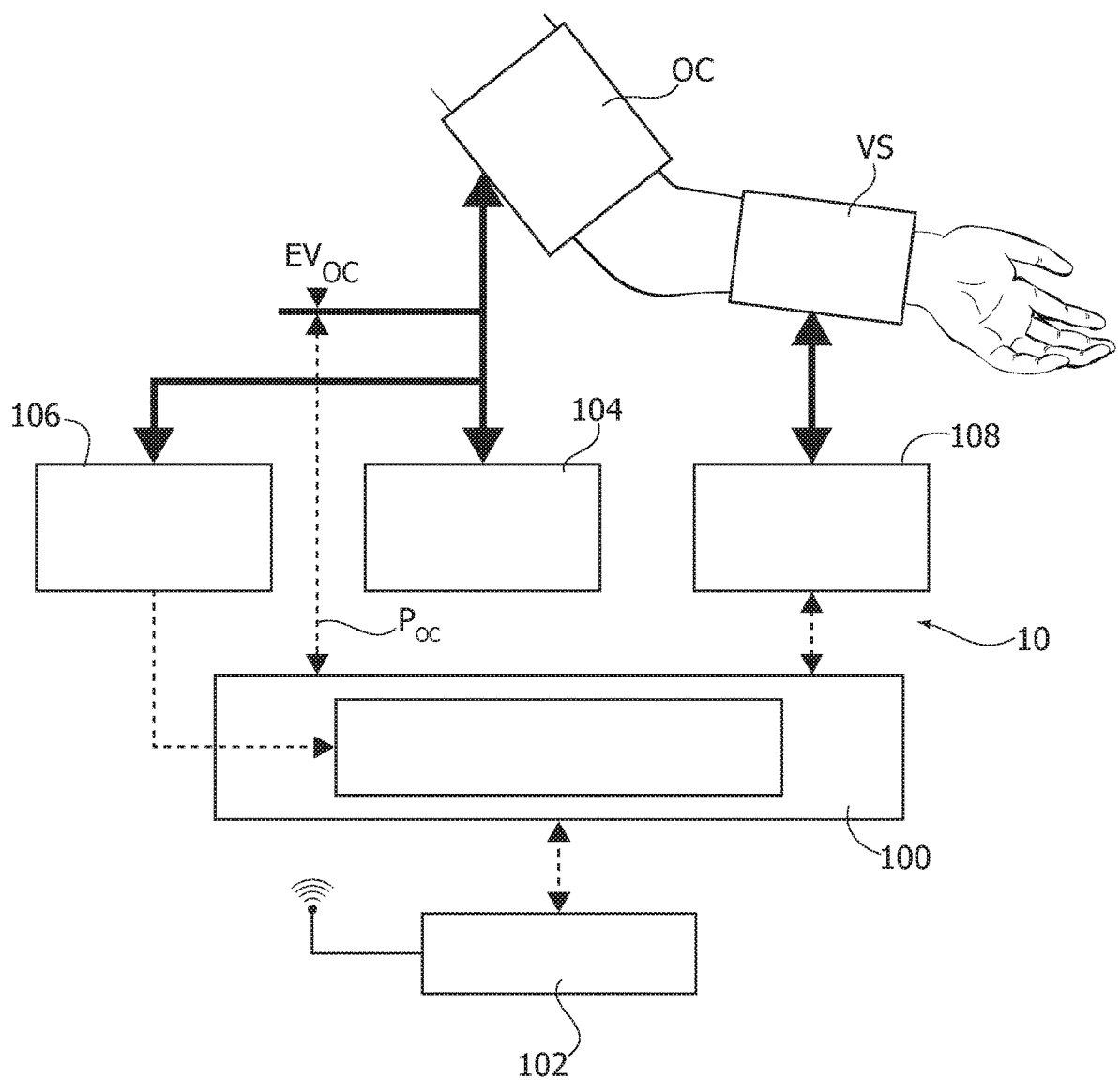
FIGS. 2 and 3 are functional block diagrams provided by way of example of possible modalities of implementation of embodiments.
Figure 3:
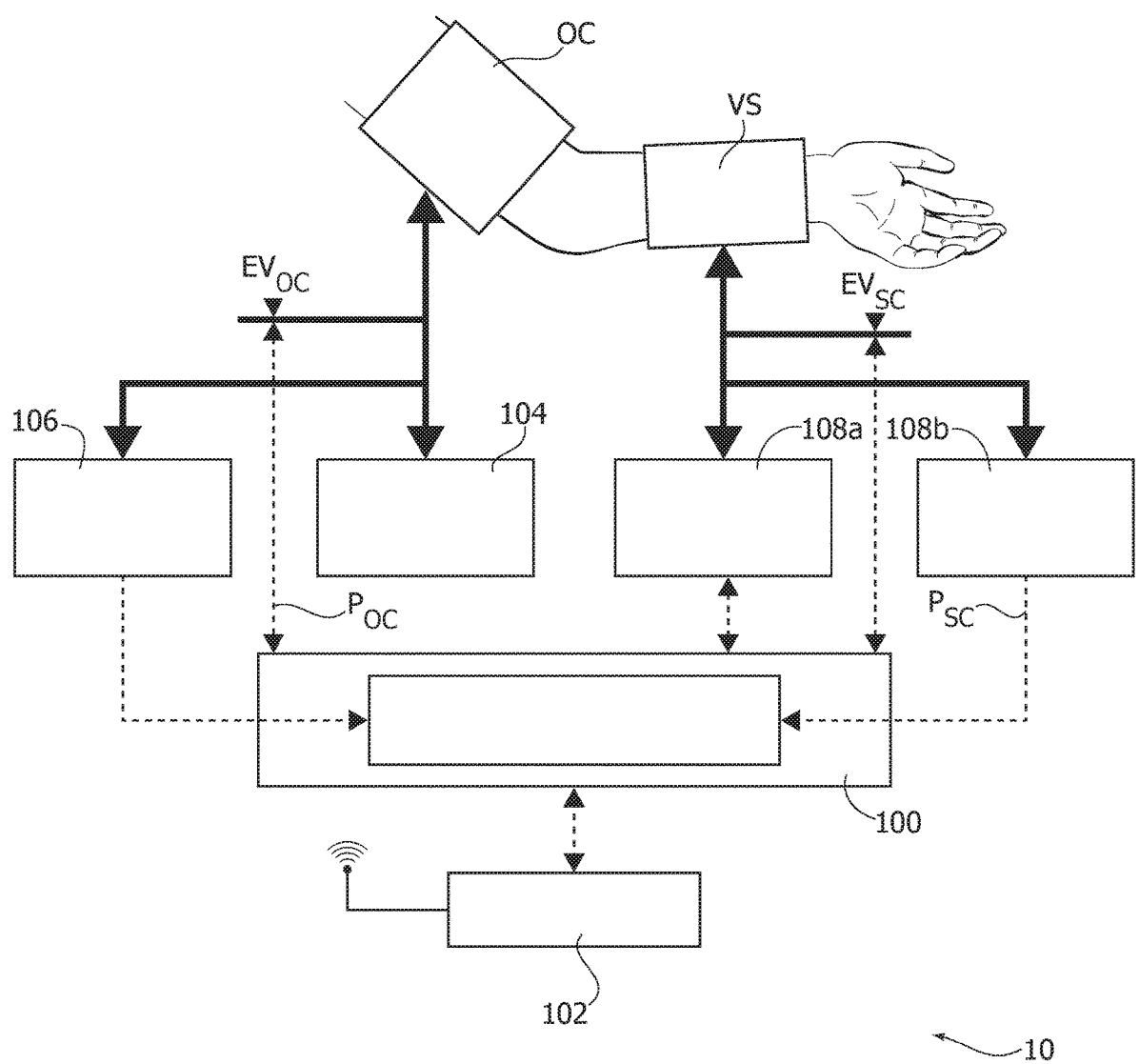
Figure 5:
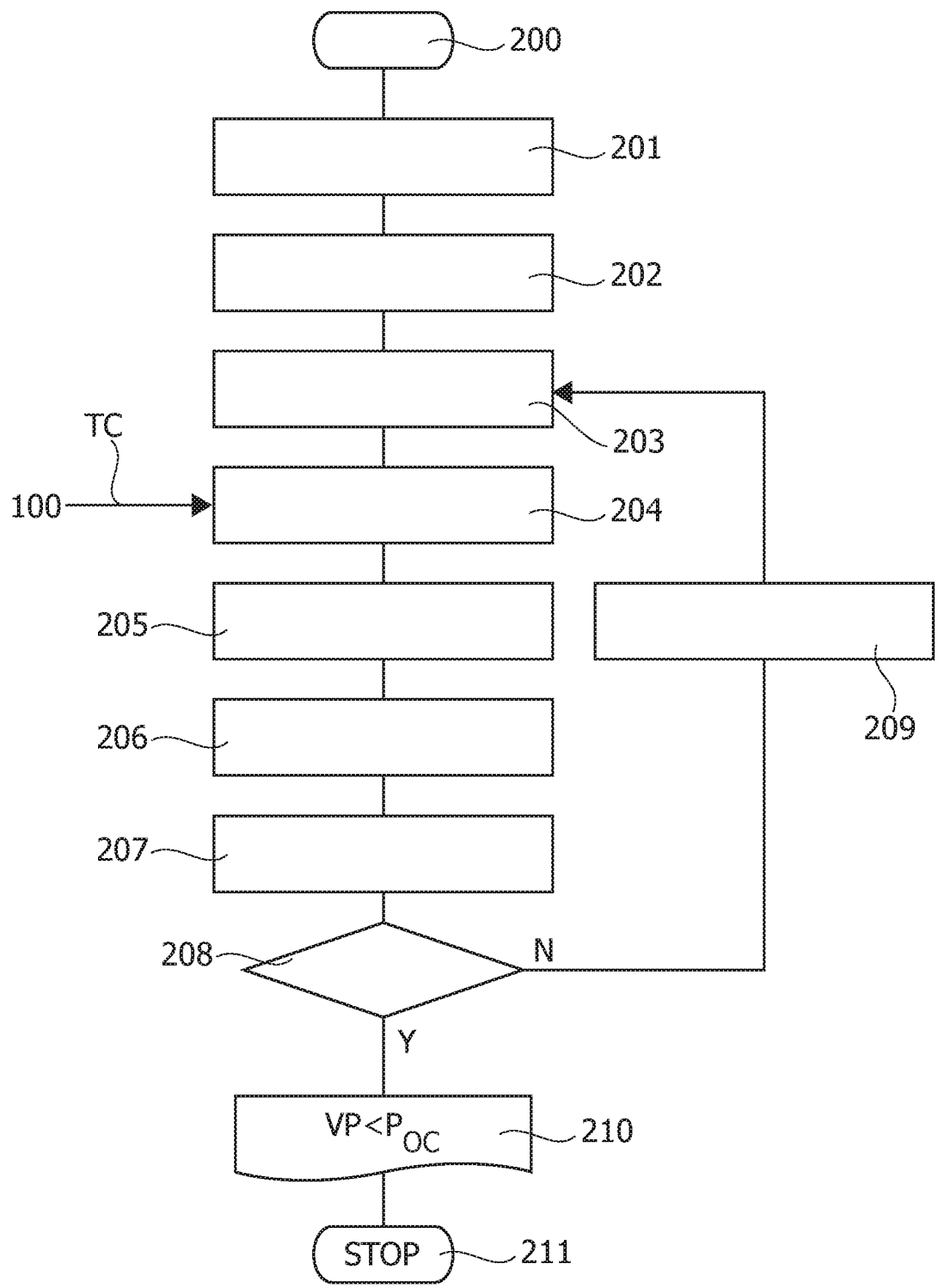
FIG. 5 is a flowchart provided by way of example of possible modalities of operation of embodiments.

As exemplified in FIGS. 2 and 3, in one or more embodiments, the signal-processing circuit 10 may comprise a signal-processing unit (CPU) 100 capable of co-ordinating the operation of the other components of the system, for example according to the flowchart of FIG. 5.

To the signal-processing unit (CPU) 100 there may be associated (according to current criteria) a display unit 102 for presenting to a user—who may be the patient P himself—various signals inherent in operation of the system and in the results of the action of detection (measurement).

As represented schematically by the symbol of an antenna in FIGS. 2 and 3, in one or more embodiments the display unit 102 may be replaced by and/or integrated with a communication interface (for example, on a mobile-communication network) in view of remote transmission of various signals inherent in operation of the system and in the results of the action of detection (measurement), according to the by now currently used modalities of so-called telemedicine.

The signal-processing circuit 10 may, on the other hand, be obtained with various modalities: for example, the signal-processing circuit 10 may be "implemented" on a personal computer or the like (for example, in the case of an apparatus for clinical use by specialized staff) or else as microprocessor or microcontroller (for example, in the case of a mobile device that can be used by the patient P himself also at home).

In one or more embodiments, the occlusion element OC may comprise a (first) pneumatic cuff that can be positioned on the proximal stretch of the limb and can be controlled by the circuit 10 (for example, via a pressure control 104 co-operating with an occlusion-pressure sensor 106) for application of occlusion pressures $P_{OC}$ with increasing programmable values (for example, in the range of about 4 to 24 mmHg or 5 to 35 mmHg).

This can occur according to criteria in themselves known to the persons skilled in the sector, for example according to criteria that substantially correspond (except for the different pressure values applied, which are sub-diastolic pressure values) to the criteria of production and use of sphygmomanometers for the measurement of arterial pressure.

By "sub-diastolic pressure values" are here meant values (for example, in the range of about 4 to 24 mmHg or 5 to 35 mmHg) such as to be clearly lower than the values of the diastolic (arterial) pressure, which may range between 60 mmHg (low pressure) and 100 mmHg (high pressure, sign of hypertension).

One or more embodiments can exploit the marked correlation between the occlusion pressure $P_{OC}$ and the venous pressure VP, which makes it possible to create, by acting on the occlusion element OC (for example, of a positionable pneumatic cuff), corresponding and precise venous pressures VP in the portion of limb distal with respect to the occlusion element OC (for example, in the forearm of the patient).

It may in fact be noted that the effect of the venous pressures VP induced by the occlusion pressure $P_{OC}$, in the case where the latter is higher than the venous pressure VP of the patient, expresses itself with a variation in volume (dilation) of the distal portion of limb, known also as rapid volume response (RVR), determined uniquely by the venous dilation conterbalanced by the resistance of the surrounding tissues.

It has likewise been noted that for an RVR to appear that can be used for reliable sensing of the venous pressure VP, in addition to the condition of the pressure $P_{OC}$ being higher than the venous pressure VP of the patient, it is advantageous to maintain the pressure $P_{OC}$ for a certain time interval $TP_{OC}$ in order to enable stabilization of the RVR.

Albeit without wishing to be tied down to any specific explanation in this regard, there is reason to deem that this mode of operation prevents incurring in the risk of altering the RVR mechanism as a result of processes of filtration of the liquids that can arise with the lengthening of the times of maintenance of the pressure $P_{OC}$.

The above time interval $TP_{OC}$ may be chosen so as to be at least some seconds long, for example at least 5 s.

It has been noted that in this way the complete manifestation of the RVR is facilitated.

In one or more embodiments, the duration of the time interval $TP_{OC}$ may be varied; for example, this duration may be chosen, possibly in an adjustable way, as a function of the sub-diastolic pressure value $P_{OC}$ applied via the occlusion element OC.

For instance, it is possible to choose $TP_{OC}$ equal to approximately 10 or 20 s for a pressure $P_{OC}$ of 5 mmHg and approximately 30 or 40 s for a pressure $P_{OC}$ of approximately 24 or 35 mmHg.

Said values of $TP_{OC}$ have proven advantageous in the case of a dilation-sensing element VS obtained, as exemplified in FIG. 1, by resorting to a cuff or sleeve.

It has likewise been noted that, by using as dilation-sensing element VS (as exemplified in FIG. 4) a photoplethysmographic sensor, which is able to consider just the increase in the volume of blood contained in the superficial veins underlying it, it is possible to reduce the duration of the time interval $TP_{OC}$ also to a few seconds (for example, approximately 5 to 10 s) and not more than a few tens of seconds (i.e., approximately 20 to 40 s).

Figure 4:
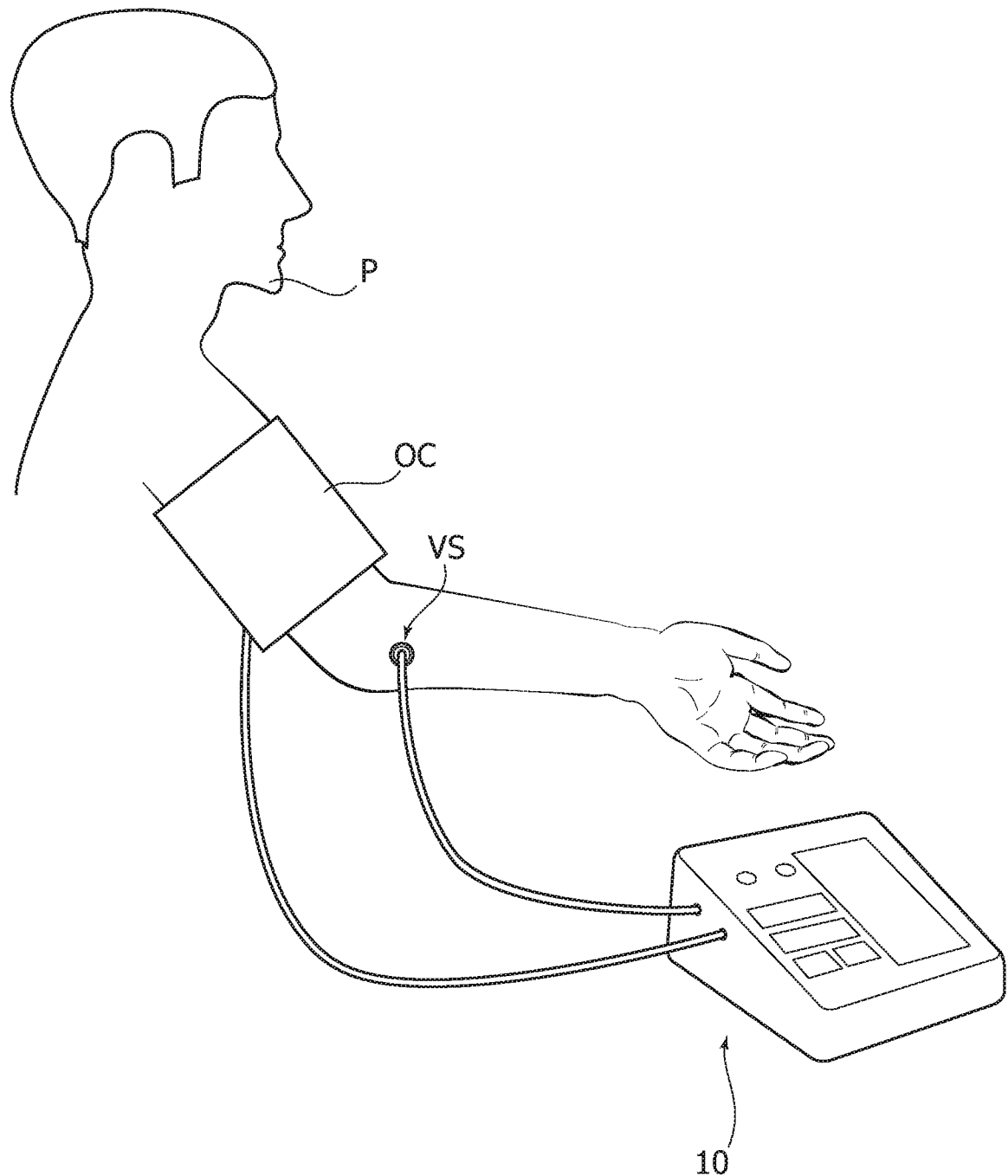
FIG. 4 provides an example of the possibility of adopting different modalities of implementation for one or more embodiments.

It will on the other hand be noted that the ones exemplified in FIG. 1 (cuff-type or sleeve-type sensor VS) and in FIG. 4 (photoplethysmographic-type sensor VS) are just two of a number of possible embodiments of the aforesaid dilation-sensing element: the dilation-sensing element VS can in fact be obtained in various ways, for example resorting to pneumatic cuffs for pressure measurement, photoplethysmographic sensors, strain gauges, piezoelectric sensors, impedance meters, inductive systems, capacitive systems, and ultrasound systems.

Whatever the technological choice adopted in this regard (pressure sensor, photoplethysmographic sensor, or whatever), in one or more embodiments, the dilation-sensing element VS may be configured for detecting the increase in volume (RVR) that may or may not arise in relation to the fact that the pressure $P_{OC}$ applied is higher or lower than the venous pressure VP of the patient.

A possible embodiment of the dilation-sensing element VS may envisage the use of a (second) pneumatic cuff—structurally similar to the one used for obtaining the occlusion element OC—which can be positioned on the forearm and pre-loaded to a pressure lower than the normal values of the venous pressure VP, for example 3 mmHg, for making a measurement of pressure ($P_{SC}$) that will be able to provide an indirect measurement of the RVR.

Such a mode of use may be implemented via a volume control/sensor co-operating with the circuit 100 and represented by block 108 in FIG. 2, whereas FIG. 3 exemplifies the possibility of resorting (once again for the purposes of detecting a possible dilation of the distal stretch of the limb) to a detection of the pressure $P_{SC}$ implemented via a pressure control 108a and a pressure sensor 108b.

A device according to one or more embodiments may consequently envisage a comparison of the pressure value $P_{SC}$ detected in an adequate time interval immediately prior to the end of the programmed time interval $TP_{SC}$ with the pressure value $P_{SC}$ detected in an adequate time interval immediately subsequent to removal or release of the pressure $P_{OC}$.

The above removal or release of the pressure $P_{OC}$ may occur, for example, following upon emptying of the occlusion element OC, if this is in the form of a cuff or sleeve.

In this regard, it will be appreciated that "removal" of the occlusion pressure $P_{OC}$ does not involve in any way—even merely implicitly—removal of the occlusion element OC from the limb: as has been said, for example in the case where recourse is had to an occlusion cuff or sleeve, removal or release of the occlusion pressure may simply involve deflation of the occlusion cuff or sleeve, which is left on the limb, for example in order to apply a higher occlusion pressure as discussed more fully in what follows.

A device according to one or more embodiments may consequently, envisage verifying whether there occurs a drop in the pressure signal $P_{SC}$ (i.e., a reduction having a value greater than a programmable threshold, e.g., 0.1 mmHg), which expresses a reduction in the RVR following upon release of the occlusion and consequently the fact that the venous pressure VP of the patient is lower than the occlusion pressure value $P_{OC}$ applied.

A device according to one or more embodiments may consequently envisage checking for the possible occurrence of different situations.

For instance:

if a drop is detected in the pressure signal $P_{SC}$ (i.e., with a reduction in the dilation of the distal stretch of the limb induced by the pressure $P_{OC}$ applied) the device will indicate—for example, via the unit 102—that the venous pressure VP is lower than X mmHg (with X mmHg corresponding to the value of pressure $P_{OC}$ set for this test);

if, instead, such a drop in the pressure signal $P_{SC}$ is not detected (i.e., no reduction in the degree of dilation of the distal stretch of the limb is detected), the device will indicate—once again, for example, via the unit 102—that the venous pressure VP is higher than the occlusion pressure $P_{OC}$ applied, and automatically or after prior consent the test will be repeated with a subsequent value of XX mmHg of the occlusion pressure $P_{OC}$, higher than the value of X mmHg programmed by the system.

By adopting the same basic criteria, given a threshold represented for example by a range (ThresholdMin=0.10 mmHg and ThresholdMax=0.15 mmHg):

if a drop is detected in the pressure signal $P_{SC}$ (i.e., with a reduction in the dilation of the distal stretch of the limb induced by the pressure $P_{OC}$ applied) comprised between ThresholdMin and ThresholdMax, then the outcome is positive ("ON response") and the device will indicate—for example, via the unit 102—that the venous pressure VP is equal to X mmHg (with X mmHg corresponding to the pressure value $P_{OC}$ set for this test);

- if a drop is detected in the pressure signal $P_{SC}$ that is greater than ThresholdMax, then the outcome is positive ("ON response") and the device will indicate—for example, via the unit 102—that the venous pressure VP is lower than X mmHg (with X mmHg corresponding to the pressure value $P_{OC}$ set for this test);
- if, instead, no drop is detected in the pressure signal $P_{SC}$, i.e., $P_{SC}$<ThresholdMin, then the outcome is negative ("OFF response", i.e., no reduction is detected in the degree of dilation of the distal stretch of the limb), the device will indicate—once again, for example, via the unit 102—that the venous pressure VP is higher than the occlusion pressure $P_{OC}$ applied and, automatically or after prior consent, the test will be repeated with a subsequent value of XX mmHg of the pressure $P_{OC}$, higher or lower than the value of X mmHg programmed by the system.

In simple terms, if the occlusion pressure applied $P_{OC}$ is lower than the existing venous pressure VP, nothing happens: the distal stretch of the limb does not increase in volume as occurs, instead, if the occlusion pressure applied $P_{OC}$ is higher than the existing venous pressure VP.

The check on the increase or absence of increase in the degree of dilation (volume) following upon application of the occlusion pressure $P_{OC}$— taken at the end of a certain interval $TP_{OC}$—for example, at the moment of removal or release of the pressure $P_{OC}$ (for example, by deflating the occlusion sleeve or cuff OC)—enables the possible increase in dilation to be ascertained in a state of stable equilibrium with respect to the time constants involved.

For instance, after inflation of the sleeve or cuff OC so as to apply an occlusion pressure $P_{OC}$, at the end of the period of equilibrium $TP_{OC}$ (equal, for example, to approximately 10 s or else 20 s), the occlusion pressure $P_{OC}$ is removed by deflating the sleeve or cuff OC.

At this point:

- if the occlusion pressure $P_{OC}$ applied via the sleeve or cuff OC is higher than the venous pressure VP, the sensor VS detects a reduction in degree of dilation (volume), which indicates the fact that pressure $P_{OC}$ is higher than the venous pressure VP;
- if the occlusion pressure $P_{OC}$ applied via the sleeve or cuff OC is lower than the venous pressure VP, the sensor VS will detect a reduction in degree of dilation (volume) that is zero (or lower than a minimum pre-defined threshold), which indicates a pressure $P_{OC}$ lower than the venous pressure VP: there is, in fact, no reason why the limb should increase in volume if the pressure $P_{OC}$ is lower than the venous existing pressure.

In the case where the repetition of the test has a positive outcome for the new occlusion pressure $P_{OC}$ set (XX mmHg), the system will indicate that the venous pressure VP is lower than XX mmHg and higher than X mmHg or else the venous pressure VP is comprised between XX mmHg and X mmHg.

It will be appreciated that the amplitude of variation of pressure between XX mmHg and X mmHg (and possible other subsequent tests) identifies the resolution of the action of detection or measurement adopted.

Altogether similar considerations apply to possible embodiments, as exemplified in FIG. 4 (dilation-sensitive element VS provided as a photoplethysmograph).

For instance, by applying, via the occlusion element OC, an occlusion pressure $P_{OC}$ (for example, a pressure of 8 mmHg, which is sub-diastolic or in any case lower than the arterial pressure, which is normally of approximately 120 mmHg, maintaining it for a certain interval $TP_{OC}$, and then bringing it back rapidly to zero (hence removing the occlusion pressure), there may be noted two different behaviours of the photoplethysmographic-type sensor VS:

- if the occlusion pressure $P_{OC}$ is higher than the venous pressure VP, a signal generated by the sensor VS will be noted, which indicates the fact that the veins downstream of the occlusion element OC have increased in volume owing to occlusion of the return flow and that, by removing the pressure $P_{OC}$, the return venous flow has been restored, with a consequent reduction in volume of the aforesaid veins, with a (rapid) reduction in volume that brings the signal of the sensor VS back to zero (or to a reference level);
- if the pressure $P_{OC}$ is lower than the venous pressure VP, in the signal of the sensor VS no evolution of the type described will be observed: since the occlusion pressure $P_{OC}$, set via the occlusion element OC, is lower than the venous pressure VP, the return venous flow from the distal stretch of the limb is not appreciably occluded by the occlusion pressure $P_{OC}$, so that there is no increase in volume of the veins that can be detected once the occlusion pressure $P_{OC}$ is removed.

Also in this case, with consecutive measurements at different values of occlusion pressure $P_{OC}$ it will be possible to determine with successive approximations the value of venous pressure VP with a degree of approximation that is sufficient/acceptable for a clinical diagnosis.

The flowchart of FIG. 5 exemplifies possible modalities of operation of embodiments: in this regard, it will be appreciated that the actions exemplified in the flowchart of FIG. 5 (just to provide a non-limiting example, the possibility of varying selectively the duration of the time interval $TP_{OC}$ as a function of the pressure $P_{OC}$ applied—signal TC at input to block 204) are to a large extent irrespective of the specific choices of implementation, for example at the level of the dilation-sensing element VS.

The blocks of FIG. 5 exemplify the possible actions listed below:

- 200: start (START);
- 201: set the dilation-sensing element VS to a baseline value;
- 202: determine a (sub-diastolic) value of occlusion pressure $P_{OC}$, starting from an initial minimum value;
- 203: apply the aforesaid value of occlusion pressure $P_{OC}$ to the proximal stretch of the limb via the occlusion element OC;
- 204: maintain the aforesaid value of occlusion pressure $P_{OC}$ for a wait time $TP_{OC}$, which may be variable, for example adjustable as a function of the value of pressure applied (signal TC from the circuit 100);
- 205: remove the occlusion, for example, by (at least partial) deflation of the occlusion element OC;
- 206: detect a possible variation of the dilation of the distal stretch of the limb via the control 108 (or 108*a*, 108*b*) associated to the sensor VS (for example, via the pressure value $P_{SC}$ detected in block 108*b* immediately prior to the end of a programmed time interval $TP_{SC}$, with the pressure value $P_{SC}$ being detected in an adequate time interval immediately subsequent to completion of deflation of the occlusion element OC);

207: reset the dilation-sensing element VS to a baseline value, for example, following upon (at least partial) deflation of the corresponding cuff;

208: compare the value detected in block 206 with a threshold Th to verify whether an appreciable variation of the degree of dilation of the distal stretch of the limb has occurred or not, for example a certain drop in the pressure signal $P_{SC}$;

209: in the case of a negative outcome (N) of the comparison made in block 208 (i.e., the distal stretch of the limb has not dilated in so far as the occlusion pressure $P_{OC}$ applied is lower than the venous pressure VP), reset the (sub-diastolic) value of occlusion pressure $P_{OC}$ to a value higher than the one previously applied (passage from X mmHg to XX mmHg in the case of the example seen previously);

210: in the case of a positive outcome (Y) of the comparison made in block 208 (i.e., the distal stretch of the limb, after removal of the occlusion pressure $P_{OC}$, tends to reduce its degree of dilation after being previously dilated in so far as the occlusion pressure $P_{OC}$ applied is higher than the venous pressure VP), indicate that the pressure VP is lower than the value of occlusion pressure $P_{OC}$, (VP<$P_{OC}$) previously applied (X mmHg, in the case of the example seen previously);

211: end (STOP)

One or more embodiments may consequently envisage application (for example, in the upper part of the arm) of a sequence of square-wave pulses of occlusion pressure ($P_{OC}$) with increasing amplitude.

At each pulse, the amplitude of the pressure $P_{OC}$ is maintained constant for a given occlusion time ($TP_{OC}$) such as to favour stabilization of the rapid volume response (RVR) in the forearm. At each pulse, after the stabilization time, the pressure $P_{OC}$ is set to zero, and the RVR is evaluated: when a significant variation of the RVR is detected (for example, via a threshold check), it is determined that the venous pressure (VP) is lower than the amplitude of the pressure pulse $P_{OC}$ applied. If no significant change in the RVR is detected, the procedure continues by applying a subsequent pressure pulse $P_{OC}$ with an increased programmed amplitude. The procedure is repeated until a significant variation of the RVR is noted, thus identifying the pressure value $P_{OC}$ that corresponds to the venous pressure VP.

The resulting venous pressure VP is obtained from the amplitude of a single constant pulse of the pressure $P_{OC}$.

This aspect is important in so far as it facilitates a reliable determination of the value VP, it being possible to take into account the physiological time constant Tau (depending upon the vein/tissue compliance of the patient) in order to have a significant and stable RVR (see, for example Gamble J., Gartside I., Christ F., "A reassessment of mercury in silastic strain gauge plethysmography for microvascular permeability assessment in man", *J. Physiol.* 1993 May; 464: 407-22, already cited previously).

The experiments conducted by the present applicant have highlighted reasons of advantage linked to various possible aspects of embodiments.

For instance, it has proven advantageous to be able to determine the time of maintenance of the occlusion pressure $TP_{OC}$, with this wait time that is sufficiently long (for example, some tens of seconds) to facilitate reaching of a condition of stable RVR (as expressed by $P_{SC}$, for example) determined by the compliance of the veins and of the surrounding tissues mechanically involved in dilation, without reaching values of some minutes long, such as to lead to an alteration of the interstitial volume secondary to filtration of the fluids by the veins themselves.

It has likewise proven advantageous to be able to vary the time $TP_{OC}$ as a function of the value of the occlusion pressure $P_{OC}$ (see the signal TC in FIG. 5).

As has been said, useful values may range, for example, from approximately 10 s or 20 s of $TP_{OC}$ for approximately 5 mmHg of $P_{OC}$ up to approximately 30 or 40 s of $TP_{OC}$ for approximately 24 or 35 mmHg of $P_{OC}$, with other possible values in proportion.

In this way, it is possible to reduce the times of the test, which, in particular for the test (statistically the most frequent one) at 10 mmHg, may become very short, with evident advantages for users.

Likewise, and as has already been said, using as dilation-sensing element (VS in the figures) a photoplethysmographic sensor, which will be able to consider just the increase in volume of the blood contained in the superficial veins underlying it, it is possible to reduce the duration of the time interval $TP_{OC}$ (given the same applied occlusion pressures) even to a few seconds and to not more than some tens of seconds.

As regards the procedure of calculation of the drop in pressure $P_{SC}$ (action 206 in FIG. 4) it is possible, for example, to compute the difference between the average of the pressure values $P_{SC}$ detected in a certain time interval prior to the command for deflation of the occlusion element OC (action 205 in FIG. 4) and the average of the values of the pressure $P_{SC}$ detected after deflation of the occlusion element OC.

Again, the logic of automatic increase of the pressure $P_{OC}$ (action 209 in FIG. 5) could follow different rules, both with the aim of identifying simply value ranges of VP (low, normal, borderline, high, very high) and with the possibility of adopting a fine increment step, and hence a fine resolution, according to the needs.

For instance, assuming adoption, for the comparison of the action 208 of FIG. 4, of a threshold such that:

if the pressure $P_{SC}$ varies, at the value $P_{OC}$, by 10 mmHg, then there is no drop (negative outcome from block 208); and the pressure $P_{SC}$ varies, at the pressure $P_{OC}$, by 15 mmHg, then there is a drop (positive outcome from step 208), it is possible to program, in the action 209 of FIG. 4, a subsequent measurement at 12.5 mmHg, which facilitates obtaining a higher measurement definition or resolution.

There has likewise been noted the advantage linked to the use of a cuff (sleeve—the terms can here be considered as synonyms) VS pre-loaded at a starting pressure (e.g., 3 mmHg) and/or pre-expanded by the presence of foam rubber. It has been noted that the presence of material such as foam rubber facilitates even distribution of the pressure in contact with the limb, without any need to apply a starting pressure level, as discussed previously.

There has likewise been noted the advantage linked to the use of sleeves (or cuffs) OC and/or VS that adopt a mechanism for pre-tensioning at a pre-set tightness in order to facilitate an adequate positioning thereof.

As in conventional procedures, in electronic sphygmomanometers, it is likewise possible to envisage implementation of software control systems (based upon computation of the times required for reaching pre-defined target pressure values) for detecting conditions of positioning of the sleeves that are too loose and/or too tight.

In a device as exemplified herein there may also be integrated the possibility of making, in addition to the measurement of venous pressure, also a standard measurement of systolic and diastolic arterial pressure.

A device as exemplified herein may comprise:
- an occlusive element (for example, OC) configured for being applied to a proximal portion of a human limb in order to apply an occlusion pressure thereto;
- a dilation-sensing element (for example, VS) configured for being applied to a distal portion of a human limb in order to detect an extent of dilation thereof; and
- a control circuit (for example, 10) coupled to the occlusive element and to the dilation-sensing element, the control circuit being configured for:
  i) controlling (for example, 104, 106) the occlusive element in order to apply (for example, 203) at least one sub-diastolic occlusion pressure (for example, $P_{OC}$) and maintaining (for example, 204) said at least one sub-diastolic occlusion pressure for a certain occlusion interval (for example, $TP_{OC}$);
  ii) obtaining (for example, 108; 108a, 108b) a sensing signal from the dilation-sensing element;
  iii) carrying out a check (for example, 208) on said sensing signal for a certain variation of the dilation of said distal portion of a human limb resulting from the fact that said at least one sub-diastolic occlusion pressure is removed (or released, for example by deflating an occlusion sleeve or cuff) after said occlusion interval; and
  iv) issuing a signal (for example, 102, 210) indicating a venous pressure in said human limb that is lower than said at least one sub-diastolic occlusion pressure applied as a result of the fact that said check indicates a certain variation of the dilation of said distal portion of a human limb resulting from the fact that said at least one sub-diastolic occlusion pressure is removed after said occlusion interval.

As has already been said, "sub-diastolic pressure" is here intended to indicate a pressure having values (for example, in the range of about 5 to 35 mmHg or else 4 to 24 mmHg) such as to be clearly lower than the values of the diastolic (arterial) pressure, which may range between 60 mmHg (low pressure) and 100 mmHg (high pressure, sign of hypertension).

In a device as exemplified herein, with said check failing to indicate said certain variation of the dilation of said distal portion of a human limb resulting from the fact that said at least one sub-diastolic occlusion pressure is removed after said occlusion interval, said control circuit may be configured for repeating said actions i) to iv) by controlling the occlusive element in order to apply at least one further occlusion pressure higher than said at least one sub-diastolic occlusion pressure.

In a device as exemplified herein, said occlusion interval may have a duration of not less than 5 s, optionally between about 10 s and about 30 s, or else between about 20 s and about 40 s (for example, with an element VS provided as pressure sensor) or else between about 5 s and about 10 s (for example, with an element VS provided as photoplethysmographic sensor).

In a device like the one exemplified herein, the control circuit may be configured for controlling the occlusive element in order to apply occlusion pressures in the range of about 5 mmHg to 35 mmHg, or else of about 4 mmHg to 24 mmHg.

In a device as exemplified herein, the control circuit may be configured (for example, TC in FIG. 5) for varying the duration of said occlusion interval, optionally as a function of the occlusion pressures applied.

In a device as exemplified herein, said dilation-sensing element may comprise a pressure sensor (for example, VS, 108a, 108b in FIG. 3), wherein said sensing signal comprises a pressure signal ($P_{SC}$).

In a device as exemplified herein, said dilation-sensing element (for example, VS in FIG. 4) may comprise a photoplethysmographic sensor, wherein said sensing signal comprises a photoplethysmographic signal, indicating the variations of the volume of the superficial veins underlying it.

In a device as exemplified herein, the control circuit may be configured for detecting (for example, 208) in said sensing signal (for example, pressure-sensing signal or plethysmographic sensing signal) a variation of an amount greater than a variation threshold (for example, a drop in pressure of an amount greater than a certain pressure-drop threshold), and issuing said signal (for example, 102, 210) indicating a venous pressure in said human limb that is lower than said at least one sub-diastolic occlusion pressure (VP<$P_{OC}$) as a result of detection, in said sensing signal, of a variation of an amount greater than said variation threshold.

In a device as exemplified herein, at least one between said occlusive element and said dilation-sensing element may comprise a cuff configured for being applied on a human limb, said cuff being optionally pre-expanded and/or pre-loaded to a certain wrapping tightness.

Without prejudice to the underlying principles, the details of construction and the embodiments may vary, even significantly, with respect to what has been illustrated herein purely by way of non-limiting example, without thereby departing from the extent of protection, as this is determined by the annexed claims.

The invention claimed is:

1. A device for measuring venous pressure, comprising:
   - an occlusive element configured to be applied onto a proximal portion of a human limb to apply an occlusion pressure thereto,
   - a dilation sensing element configured to be applied onto a distal portion of the human limb to sense an extent of dilation thereof,
   - a control circuit coupled to the occlusive element and the dilation sensing element, the control circuit configured to:
     i) control the occlusive element to apply at least one sub-diastolic occlusion pressure and maintain said at least one sub-diastolic occlusion pressure ($P_{OC}$) for an occlusion interval,
     ii) obtain from the dilation sensing element a sensing signal,
     iii) perform a check of said sensing signal for a certain variation of the dilation of said distal portion of the human limb resulting from said at least one sub-diastolic occlusion pressure being removed after said occlusion interval,
     iv) as a result of said check indicating said certain variation of the dilation of said distal portion of the human limb resulting from said at least one sub-diastolic occlusion pressure being removed after said occlusion interval, issue a signal indicating that a venous pressure in said human limb is lower than said at least one sub-diastolic occlusion pressure applied, and
     v) as a result of said check failing to indicate said certain variation of the dilation of said distal portion of the human limb resulting from said at least one sub-diastolic occlusion pressure being removed after said occlusion interval, repeat at least i) to iii) by controlling the occlusive element to apply another sub-diastolic occlusion pressure that is higher than a prior sub-diastolic occlusion pressure.

2. The device of claim 1, wherein said occlusion interval has a duration not shorter than 5 seconds.

3. The device of claim 1, wherein the control circuit is configured to control the occlusive element to apply occlusion pressures in a range of 5 mmHg to 35 mmHg or 4 mmHg to 24 mmHg.

4. The device of claim 2, wherein the duration is between 10 and 30 seconds.

5. The device of claim 2, wherein the duration is between 20 and 40 seconds.

6. The device of claim 2, wherein the duration is between 5 and 10 seconds.

7. The device of claim 1, wherein the control circuit is configured to vary a duration of said occlusion interval.

8. The device of claim 7, wherein the control circuit is configured to vary the duration of said occlusion interval as a function of the occlusion pressures applied.

9. The device of claim 1, wherein said dilation sensing element comprises a pressure sensor, wherein said sensing signal comprises a pressure signal.

10. The device of claim 1, wherein said dilation sensing element comprises a photoplethysmographic sensor, wherein said sensing signal comprises a photoplethysmographic signal.

11. The device of claim 1, wherein the control circuit is configured to detect in said sensing signal a variation of an amount in excess of a variation threshold and issue said signal indicating the venous pressure in said human limb which is lower than said at least one sub-diastolic occlusion pressure as a result of detecting in said sensing signal the variation of the amount in excess of said variation threshold.

12. The device of claim 1, wherein at least one of said occlusive element and said dilation sensing element comprises a cuff configured to be applied on the human limb.

13. The device of claim 12, wherein the cuff is pre-expanded and/or pre-biased at a certain wrapping strength.

* * * * *